(12) United States Patent
Hausman et al.

(10) Patent No.: US 11,344,250 B2
(45) Date of Patent: *May 31, 2022

(54) PERCUTANEOUS STIMULATION DEVICE AND METHOD FOR DETECTING COMPARTMENT SYNDROME

(71) Applicant: CHECKPOINT SURGICAL, INC., Cleveland, OH (US)

(72) Inventors: Michael Hausman, New York, NY (US); Robert Strother, Willoughby, OH (US); Jonathan Sakai, Fairview Park, OH (US)

(73) Assignee: CHECKPOINT SURGICAL, INC., Cleveland, OH (US)

( * ) Notice: Subject to any disclaimer, the term of this patent is extended or adjusted under 35 U.S.C. 154(b) by 301 days.

This patent is subject to a terminal disclaimer.

(21) Appl. No.: 16/594,322

(22) Filed: Oct. 7, 2019

(65) Prior Publication Data

US 2020/0029888 A1 Jan. 30, 2020

Related U.S. Application Data

(63) Continuation of application No. 14/704,690, filed on May 5, 2015, now Pat. No. 10,433,785.

(Continued)

(51) Int. Cl.
*A61B 5/00* (2006.01)
*A61B 5/03* (2006.01)
(Continued)

(52) U.S. Cl.
CPC .............. *A61B 5/4519* (2013.01); *A61B 5/03* (2013.01); *A61B 5/05* (2013.01); *A61B 5/1104* (2013.01);
(Continued)

(58) Field of Classification Search
CPC combination set(s) only.
See application file for complete search history.

(56) References Cited

U.S. PATENT DOCUMENTS 4,711,248 A * 12/1987 Steuer ...................... A61B 5/03
600/546
4,807,643 A 2/1989 Rosier
(Continued)

OTHER PUBLICATIONS

Shadgan et al. "Diagnostic Techniques in Acute Compartment Syndrome of the Leg," Orthop Trauma. (Sep. 2008).
(Continued)

*Primary Examiner* — Scott Luan
(74) *Attorney, Agent, or Firm* — McDonald Hopkins LLC

(57) ABSTRACT

A diagnosis device, and more particularly, a compartment syndrome diagnostic device is described herein. The diagnostic device may include a display that renders information associated with stimulation of a motor unit suspected of suffering from compartment syndrome. The diagnostic device may generate a stimulation signal for stimulating the motor unit through an electrode. The device may determine whether the motor unit is at risk for compartment syndrome based on the response of the motor unit to the stimulation. The diagnostic device may also measure pressure of a compartment. The device may determine whether the motor unit is at risk for compartment syndrome based on the measured pressure and the response of the motor unit to the stimulation.

17 Claims, 12 Drawing Sheets

Related U.S. Application Data

(60) Provisional application No. 61/988,665, filed on May 5, 2014.

(51) Int. Cl.
| | |
|---|---|
| *A61B 5/11* | (2006.01) |
| *A61B 5/05* | (2021.01) |
| *A61B 5/296* | (2021.01) |
| *A61B 5/389* | (2021.01) |

(52) U.S. Cl.
CPC ............ *A61B 5/1107* (2013.01); *A61B 5/296* (2021.01); *A61B 5/389* (2021.01); *A61B 5/6847* (2013.01); *A61B 5/6848* (2013.01); *A61B 5/6852* (2013.01); *A61B 5/742* (2013.01); *A61B 5/7405* (2013.01); *A61B 5/746* (2013.01); *A61B 5/7455* (2013.01)

(56) References Cited

U.S. PATENT DOCUMENTS

| | | |
|---|---|---|
| 2012/0010525 A1 | 1/2012 | Jacofsky et al. |
| 2013/0296733 A1 | 11/2013 | Strother et al. |
| 2014/0128823 A1 | 5/2014 | Odland et al. |

OTHER PUBLICATIONS

Matsen et al. "Diagnosis and Management of Compartmental Syndromes," The Journal of bone and Joint Surgery. (1980).
Sheridan et al. "Further Investigations on the Pathophysiology of the Compartmental Syndrome," Clin Orthop Relat Res. (1977).

\* cited by examiner

PERCUTANEOUS STIMULATION DEVICE AND METHOD FOR DETECTING COMPARTMENT SYNDROME

CROSS-REFERENCE TO RELATED APPLICATION

This application is a continuation of U.S. patent application Ser. No. 14/704,690 filed May 5, 2015 and entitled "PERCUTANEOUS STIMULATION DEVICE AND METHOD FOR DETECTING COMPARTMENT SYNDROME" which claims the benefit of U.S. Provisional Patent Application Ser. No. 61/988,665, filed May 5, 2014, and entitled "PERCUTANEOUS STIMULATION DEVICE AND METHOD FOR DETECTING COMPARTMENT SYNDROME," each of which are incorporated herein by reference in their entirety.

FIELD OF USE

This invention relates to a device and a method for detecting compartment syndrome.

BACKGROUND OF THE INVENTION

Compartment syndrome is a common condition where a traumatic or crushing injury causes muscle swelling, raising the tissue pressure in one of the body's compartments, such as an arm, leg or other enclosed space within the body. The increased tissue pressure begins a cycle in which the circulation is impaired, leading to higher pressures, which further decrease circulation, perpetuating the cycle. If the cycle is not treated by a fasciotomy (in which a large incision is used to relieve pressure in the extremity), it can lead to muscle death and catastrophic loss of function.

The fascia envelope that surrounds muscle and bone is strong and relatively inelastic. Because of the strength and inelasticity of the fascia envelope, the pressure inside the compartment may significantly increase with even a small amount of bleeding into the compartment or with swelling of the muscles within the compartment. Common causes of compartment syndrome include tibial or forearm fractures, ischemic reperfusion following injury, hemorrhage, vascular puncture, intravenous drug injection, casts, prolonged limb compression, crush injuries and burns.

The clinical signs of compartment syndrome are the 5 "Ps": pain (out of proportion to the injury), paresthesias (numbness), paralysis (loss of muscle contractility), pallor (loss of pulses), tense skin and vascular congestion. Poikilothermia (loss of normal thermoregulation) can also be a symptom of compartment syndrome. The clinical presentation may be ambiguous and these signs cannot be assessed in an obtunded or unconscious patient.

Because the clinical signs can be confusing or ambiguous, particularly in early stages, compartment pressures are usually measured in order to confirm the diagnosis. Markedly elevated pressures are clearly indicative of compartment syndrome. Typically, the normal pressure inside the compartment is in the range of about 5-10 mm Hg. In cases where the compartment pressure increases to 50-60 mm Hg, there will almost certainly be tissue necrosis within the compartment due to lack of new blood perfusion. In this case, compartment release surgery (e.g., a fasciotomy) is necessary to avoid muscle death and potential catastrophic loss of function to the injured limb. This surgery involves a large incision to relieve the pressure in the injured limb and can be disfiguring. In some cases, a skin graft is required to close the incision. In addition, severe complications, including post-surgical infections, can occur. However, the risks associated with these complications are less severe than the complications associated with compartment syndrome.

There is some ambiguity and even disagreement as to what constitutes a dangerous compartment pressure reading. Some advocate a relative criterion in which the pressure is within 30 mm Hg of the diastolic blood pressure. Others recommend an absolute pressure but again there is some disagreement over whether that number should be in the high 20 mm Hg range or whether it should be higher in the mid-30 mm Hg range.

If the pressures clearly exceed the threshold, then a fasciotomy should be performed, but the challenge is whether to perform the fasciotomy when the pressure is just below the threshold (e.g., 20-25 mm Hg) and the patient only exhibits some (but not all) of the clinical signs (e.g. pain with passive extension, weakness, paralysis, or numbness). If the pressure measurement is repeated some time (e.g., 1 hour) later with no change in results, then the patient may be considered at borderline risk of compartment syndrome. Presently, the risks of compartment syndrome far outweigh the risks of fasciotomy. This leads to fasciotomies being performed that probably would not be necessary if there were a more reliable test. Fasciotomies can be disfiguring (i.e., long incisions requiring skin grafts to close) and accompanied by severe complications (e.g., infection), but the complications of fasciotomies are less severe than the complications of compartment syndrome. With more accurate information from stimulation, it may be possible to protect the at risk muscle by performing an endoscopic or minimally invasive fasciotomy without the need for a large incision.

SUMMARY OF THE INVENTION

Embodiments described herein relate to devices, systems or methods for diagnosing or detecting compartment syndrome and monitoring for severity of compartment syndrome. It is an object of this invention to provide a more reliable device and method for detecting compartment syndrome.

In an embodiment, a device may be configured for generating a stimulus signal suitable for eliciting muscle contraction of a motor unit of a compartment; and monitoring at least one stimulation parameter associated with a stimulation threshold of a motor unit of the compartment. The device may further be configured for generating a rendering of a representation of data describing a history of the at least one stimulation parameter.

In another aspect, compartment syndrome diagnosis device, comprising: a stimulation component configured to generate a stimulation signal; a probe operatively in communication with a motor unit suspected of compartment syndrome, wherein the stimulation component is further configured to stimulate the motor unit via the probe and based on the stimulation signal; an intermuscular pressure sensing component configured to measure a pressure of a compartment comprising the motor unit; and a display device configured to render a display indicating stimulation parameters associated with stimulation and pressure parameters.

Described herein is a method for diagnosing compartment syndrome, comprising: stimulating, via a device comprising a processor, a motor unit in a compartment suspected to be at risk of compartment syndrome; determining a stimulation threshold associated with activation of the motor unit; and monitoring at least one of a history of stimulation thresholds over a period of time or a history of interstitial pressure over a period of time.

BRIEF DESCRIPTION OF THE DRAWINGS

Operation of the invention may be better understood by reference to the following detailed description taken in connection with the following illustrations, wherein.

DETAILED DESCRIPTION

Figure 1:
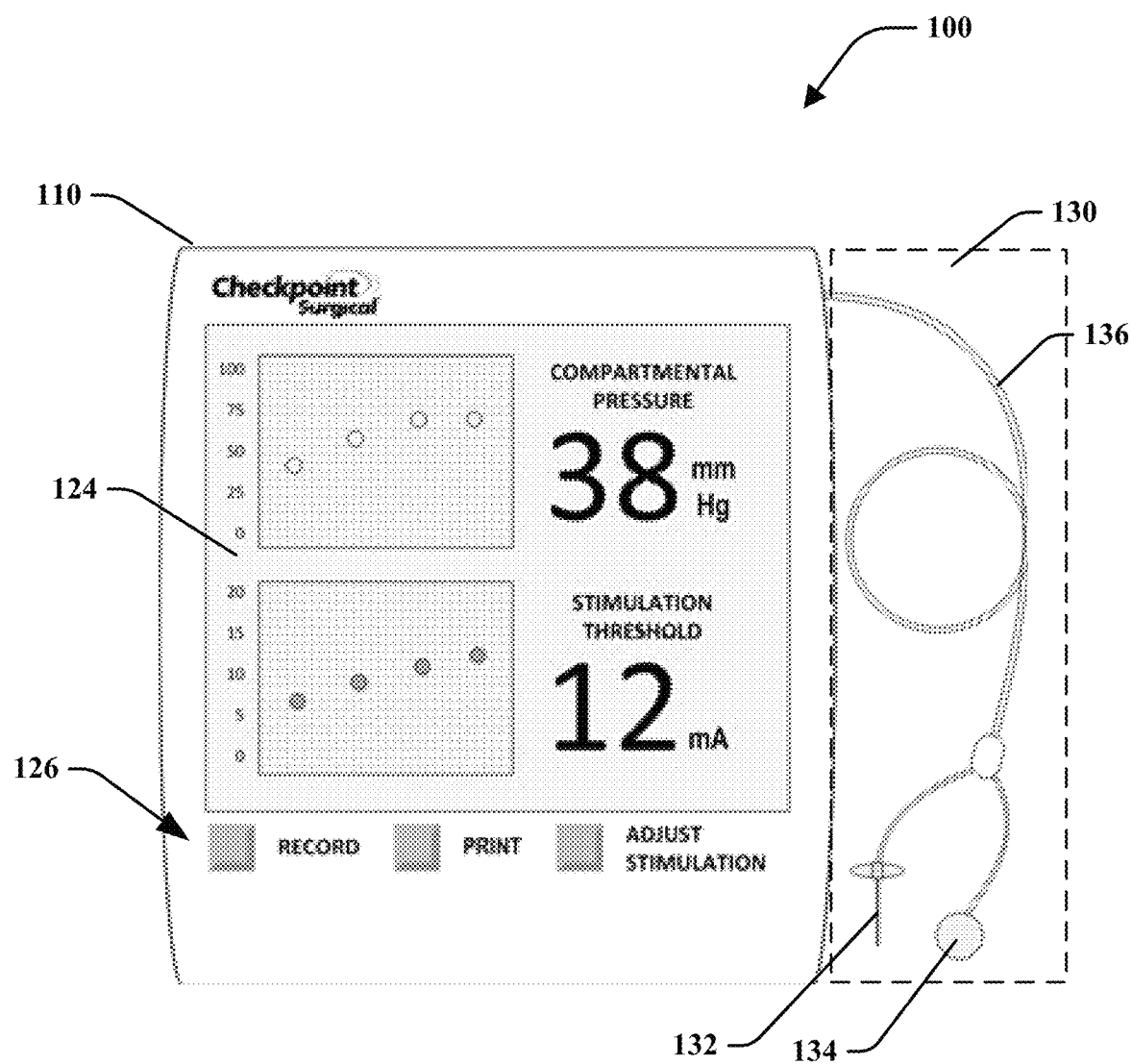
FIG. 1 is a diagnostic system for detecting compartment syndrome according to embodiments disclosed herein.

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Furthermore, the terms "patient," "subject," and the like are employed interchangeably throughout the subject specification, unless context suggests otherwise or warrants a particular distinction among the terms. It is noted that such terms may refer to an animal, such as a human, dog, horse, or the like. Likewise, terms such as "target tissue" and "motor unit" may be used interchangeably throughout, unless context suggests otherwise. Such terms may include muscle tissue, nerve tissue, muscle and nerve tissue, or the like. Moreover, examples describing stimulation of "muscle tissue" may also refer to stimulation of "nerve tissue," or a combination of both (and vice versa). It is noted, however, that such examples may list less than all possible motor units for sake of brevity.

Moreover, terms such as "doctor," "physician," "clinical worker," and the like are employed interchangeably throughout the subject specification, unless context suggests otherwise or warrants a particular distinction among the terms. Such terms may refer to an entity that may interact with a device and a patient, perform procedures, performs methods disclosed herein, and the like. Further, while embodiments and examples may describe a clinical worker or patient performing certain tasks, it is noted that a machine may perform tasks, such as through automation, logic, processors, and the like.

"Logic" refers to any information and/or data that may be applied to direct the operation of a processor. Logic may be formed from instruction signals stored in a memory (e.g., a non-transitory memory). Software is one example of logic. In another aspect, logic may include hardware, alone or in combination with software. For instance, logic may include digital and/or analog hardware circuits, such as hardware circuits comprising logical gates (e.g., AND, OR, XOR, NAND, NOR, and other logical operations). Furthermore, logic may be programmed and/or include aspects of various devices and is not limited to a single device.

Moreover, terms such as "access point," "server," "network device," and the likes, are utilized interchangeably, and refer to a network component or appliance that sends and receives data, data-streams, or signaling-streams. Data and signaling streams may be packetized or frame-based flows. A network typically includes a plurality of elements that host logic. In packet-based wide-area networks (WAN), servers (e.g., devices comprising logic) may be placed at different points on the network. Servers may communicate with other devices and/or databases.

Embodiments may utilize substantially any wired or wireless network. For instance, embodiments may utilize various radio access network (RAN), e.g., Wi-Fi, global system for mobile communications, universal mobile telecommunications systems, worldwide interoperability for microwave access, enhanced general packet radio service, third generation partnership project long term evolution (3G LTE), fourth generation long term evolution (4G LTE), third generation partnership project 2, BLUETOOTH®, ultra mobile broadband, high speed packet access, $x^{th}$ generation long term evolution, or another IEEE 802.XX technology. Furthermore, embodiments may utilize wired communications.

Aspects of systems, apparatuses or processes described herein relate to a diagnostic system for detecting medical conditions of a user. In particular, the diagnostic system may provide for or assist in detection of compartment syndrome. The diagnostic system may include a stimulation component that may monitor stimulation parameters associated with stimulation of tissue (e.g., muscle, nerve tissue, and/or both). The stimulation parameter may include a stimulation recruitment threshold, such as a stimulation intensity at which a motor unit begins to fire (e.g., muscle twitch). The stimulation component may monitor changes in stimulation parameters based on a history of the stimulation parameters.

In embodiments, the stimulation component may include a single generator that generates a stimulation signal. A single generator may be coupled to an electrode. The electrode may deliver the stimulation signal to a tissue region, such as to stimulate or attempt to stimulate the tissue. In another aspect, the electrode may be implanted on or near the tissue, on a surface above the tissue, or the like. For instance, the electrode may be disposed on a probe (e.g., needle and/or catheter), a percutaneous coiled fine wire lead, or the like.

A clinical worker, user, and/or a device (e.g., of the diagnostic system, of a separate system) may monitor tissue response to a stimulation signal. The tissue response may be entered into or received by the stimulation component.

In another aspect, the diagnostic system may include or communicate with a pressure component. The pressure component may measure a pressure in a tissue region, such as a compartment. The diagnostic system may generate alarms based on measured pressure, stimulation thresholds, or a combination thereof.

In an example, a patient may suffer a crushing or compacting injury to their arm (or other body part). The patient may experience one or more symptoms associated with compartment syndrome, such as out of proportion pain, paresthesias (numbness), paralysis (loss of muscle contractility), pallor (loss of pulses), tense skin and vascular congestion, and poikilothermia (loss of normal thermoregulation). Such symptoms may or may not be results of compartment syndrome. If compartment syndrome is left untreated, the patient may lose use of their arm or even require amputation of their arm. Accordingly, the patient may visit a medical facility for diagnosis.

A clinical worker or doctor may assess the injury and may utilize diagnostic systems and methods described herein to assist in diagnosis. For instance, the doctor may attach (e.g., implant) electrodes in a location to stimulate muscle and/or nerves (e.g., motor units in the compartment). To stimulate the tissue, the doctor may utilize a probe coupled to the diagnostic system. The doctor may set an intensity for stimulation through an interface of the diagnostic system. The doctor may then observe the tissue to determine a result of the stimulation (e.g., muscle response, no response, intensity of response, etc.). Based on the result, the doctor may adjust the intensity until a stimulation recruitment threshold is reached. The doctor may repeat the process for determining stimulation recruitment thresholds at various intervals. The diagnostic system may monitor the stimulation recruitment thresholds and present information to the doctor regarding a history of the stimulation recruitment thresholds (e.g., increase/decrease in intensity of stimulation, etc.).

It is an object of this invention to provide a more reliable device and method for detecting compartment syndrome. One aspect of the invention provides a percutaneous stimulation device for detecting compartment syndrome comprising a percutaneous intermuscular (IM) lead, an introducing needle and a portable stimulator with a skin mounted return electrode. The percutaneous IM lead is operatively connected to the portable stimulator. The system allows measuring the threshold of stimulation for muscle contractility.

In one aspect of the invention, the percutaneous stimulation device generates a single pulse every one to two seconds and records stimulus intensity that results in a visible or palpable muscle contraction (twitch). In another aspect of the invention, the percutaneous stimulation device produces a pattern of stimulation and wherein the pattern of stimulation comprises a burst of 2-4 pulses at 16 Hz repeating every 1 or 1.5 seconds. The percutaneous stimulation device may include a percutaneous combination of a pressure sensing catheter/sensor with a stimulating electrode, an introducing needle, and a portable stimulator. The stimulating electrode with the pressure sensing catheter may be capable of delivering electrical stimulation and monitoring intracompartmental pressure.

In another aspect of the invention, a method for detecting compartment syndrome is disclosed. The method comprises inserting a percutaneous lead into a muscle in a compartment of a patient suspected of having or developing compartment syndrome; establishing a threshold of stimulation intensity for visible or palpable muscle contraction; monitoring the threshold of stimulation intensity over time; and determining whether an increase in the threshold of stimulation intensity is indicative of a likelihood of developing or advancing severity of compartment syndrome.

In another aspect of the invention, in addition to establishing and monitoring the threshold of stimulation intensity, compartment pressure measurements may be taken. Assessment of the likelihood of compartment syndrome may include both the changes over time of the stimulation intensity threshold and the compartment pressure measurements. The threshold of stimulation intensity may be determined by a portable stimulator. Monitoring the threshold of stimulation intensity may be determined by monitoring the presence or absence of visible or palpable muscle contractions. The percutaneous stimulation device may also include the IM electrode or a second electrode.

Referring now to FIG. 1, there depicted is a diagnostic system 100. Diagnostic system 100 may be used to diagnose a patient, and in particular to indicate whether a patient has compartment syndrome and the severity of the compartment syndrome. Diagnostic system 100 may provide an altered level (e.g., improved level) of sensitivity and specificity in comparison with other diagnostic systems or methods. Such diagnostic systems or methods typically rely on measuring pressure with the compartment.

Pressure is an imperfect surrogate for what is really of concern as a result of compartment system, namely whether there is alteration of muscle metabolism, mitochondrial death or decreased circulation leading to muscle necrosis. Hence, contractility of the muscle in the compartment, which is of direct concern, may provide a different (e.g., improved) measure than pressure. Correct diagnosis is not academic since the treatment involves a decompressive fasciotomy which involves a long incision, a risk of wound infection and subsequent surgical procedures to close the wound, which could even necessitate the use of a skin graft, creating a second area of significant scar.

Diagnostic system 100 may include a body 110 comprising various components (e.g., power source, memory, processor, etc.) and circuitry. The body 110 may be connected (removably or irremovably) to a stimulation interface 130 comprising a signal path (e.g., wire, etc.) 136 coupled (removably or irremovably) to a probe 132 and a pressure sensor 134. It is noted that diagnostic system 100 may comprise other or different components not shown for sake of brevity. It is further noted that diagnostic system 100 may be comprised within larger systems.

The body 110 may include a display 124 and controls 126. In an example, the display 124 may include a monitor, touch screen monitor, or the like. Further, controls 126 may include input devices and/or may be comprised by the display 124. For instance, controls 126 may include buttons (pressure sensitive buttons, mechanical buttons, rocker buttons, etc.), dials, slideable controls, switches, keypads, keyboards, or the like.

In embodiments, diagnostic system 100 may be a handheld system. In a handheld system, the body 110 may include an internal power source (e.g., battery) or may be coupled with an external power source. An internal power source may include a battery. The battery may be rechargeable, such as through a power mains, universal serial bus (USB) port, power adaptor, wireless charger (e.g., near field communication charging, etc.), or the like. Further, body 110 may comprise an ergonomic design, including grips, bumpers, textured surfaces, or the likes. Such ergonomic designs may allow for increased patient and doctor satisfaction. In an aspect, diagnostic system 100 may include straps, clips, or other attachment components for attaching or securing the diagnostic system 100 to an object. For instance, a patient may utilize a clip to secure body 110 to a bed, stand, or other structure. In another example, the body 110 may be clipped, strapped, or otherwise attached to a patient or patient's clothing. By attaching to the patient, the patient may wear the body 110 for monitoring while allowing the patient to move or rest. In another aspect, body 110 may comprise lightweight materials suitable for handheld or wearable use. For instance, body 110 may comprise plastic or other material, lightweight power supplies, and the like.

Probe 132 may include a stimulation probe, needle, catheter, percutaneous stimulation lead, or other components suitable for delivering a stimulation signal. In one aspect, probe 132 may include a needle adapted to attach to a stimulation probe to allow for percutaneous stimulation. The probe 132 may be inserted on or near to a target motor unit (e.g., area of suspected compartment syndrome). In another aspect, the probe 132 may be at least partially disposable or reusable. For instance, a needle attachment may be designed for a single use while a stimulation probe may be designed for reusable applications. As such, probe 120 may comprise various different designs or configurations.

In an example, probe 132 may comprise a percutaneous (or needle) stimulation probe that may be inserted into a compartment or muscle at an injury site to assess the chance that compartment syndrome will develop and/or has developed. Diagnostic system 100 may provide a stimulation signal and the threshold of stimulation intensity for visible muscle contraction may be established by stimulation of the muscle, (e.g., through the probe 132) on the involved side or by stimulation of the contralateral compartment or muscle (e.g., same compartment/muscle on the opposite side) to establish baseline threshold and then monitoring over time (e.g., a couple of hours). In this way, the patient may serve as his/her own control. Changes in the threshold intensity (or presence/absence of a muscle contraction) could indicate changes in the compartment pressure. An increase in threshold may indicate the situation is getting worse and fasciotomy may be needed, and a decrease in threshold may indicate that a fasciotomy may not be needed.

In another example, probe 132 may include a percutaneous intermuscular (IM) lead that is placed into a target muscle near a major motor point with, for example, a hypodermic introducing needle. The percutaneous IM lead may be a coiled, threaded, braided fine wire, and the like. In an aspect, the percutaneous IM lead may be left or implanted into the muscle for repeated use. During a monitoring process, the percutaneous IM lead may be secured to the skin with, for example, an adhesive such as tape. At the end of the monitoring process, the percutaneous IM lead may be removed and discarded.

In an exemplary embodiment, diagnostic system 100 may generate an electrical stimulation signal. The stimulation signal flows from the diagnostic system 100 through a lead 136 to probe 132. The stimulation signal then flows through a predefined insulated path within the probe 132 and to an operative element, such as an electrically conductive surface, e.g., an electrode. The electrode is to be positioned in a muscle in a compartment of a patient to be stimulated. In monopolar operation, a return electrode (or indifferent electrode) provides an electrical path from the body back to the control device. The stimulation control device may operate in a monopolar or bipolar configuration.

The return electrode (e.g., a surface electrode) may be a skin-mounted electrode. The system is used to identify and record one or two thresholds of stimulation; e.g., the threshold of just palpable stimulation and a higher threshold such as visible joint motion. The pattern of stimulation employed may be a single pulse or burst of pulses (e.g., 2-4 pulses at 16 Hz repeating every 1 or 1.5 seconds). The stimulation and manual observation of the muscle response may be performed at time intervals, such as every i minutes, where i is a number (e.g., 5, 15, 30, or 45 minutes, etc.).

While embodiments describe diagnostic system 100 as measuring the threshold of stimulation, it is noted that diagnostic system 100 may include or communicate (directly or indirectly) with other systems that may measure the threshold of stimulation. Such other systems may, for example, provide stimulation to a motor unit and may communicate parameters of the stimulation (e.g., intensity, frequency, etc.) to the diagnostic system 100. For example, diagnostic system 100 may include or communicate with a stimulation device. The stimulation device may stimulate a motor unit suspected of having compartment syndrome. A doctor may adjust the intensity of stimulation to determine a threshold of stimulation. In an embodiment, the diagnostic system 100 may receive measurements and/or stimulation parameters from the stimulation device, such as through a communication network (e.g., wireless, wired, etc.) and/or through manual input. For instance, the diagnostic system 100 may receive input from a doctor. The doctor may determine values of the input based on settings or output from the stimulation device.

The configuration of the stimulation device may vary in form and function. Various representative embodiments of illustrative stimulation devices are described and depicted in U.S. Publication No. 2013/0296733, which is hereby incorporated in its entirety.

The stimulation device is adapted to provide an indication or status of the device. The indication may include a physical motor response (e.g., twitching), and/or one or more visual or audio signals from the stimulation control device, which indicate to the surgeon the status of the device, and/or close proximity of the electrode to a nerve, or a muscle, or a nerve and a muscle. The stimulation control device may also indicate to the surgeon that the stimulation control device is operating properly and delivering a stimulus current.

In an aspect, the diagnostic system 100 may include a processor or microcontroller that may operate at a low voltage and low power. The microcontroller may send a low voltage pulse to a stimulus output stage that converts these low voltage signals into the higher voltage, controlled voltage, or controlled current, stimulus pulses that are applied to the electrode circuit. This stimulus output stage usually involves the use of a series capacitor to prevent the presence of DC current flow in the electrode circuit in normal operation or in the event of an electronic component failure.

In addition to generating the stimulus bursts, the diagnostic system 100 may report the stimulus intensity. This intensity may be recorded for data trending by the diagnostic system 100. Alternatively, the intensity may be recorded by a clinician observing the stimulus or by any other appropriate recording means. The diagnostic system 100 may alert a user when it is time for the next point of monitoring. The diagnostic system 100 may also be programmed to provide a plot of the monitoring over time, such as through display 124 and/or a display in communication with diagnostic system 100, and may be wirelessly connected to a display such as a display of a desktop computer. For example, the diagnostic system 100 may be connected (e.g., wirelessly or via a wire line) to a display or computing device (e.g., tablet computer, etc.).

The diagnostic system 100 could be used in a situation in which a patient comes into the emergency department following trauma that may lead to compartment syndrome. A percutaneous lead (e.g., probe 132) may be inserted into a muscle in the compartment at risk of compartment syndrome.

In at least one embodiment, diagnostic system 100 may include a percutaneous combination of a thin fluid-filled catheter with a stimulating electrode that may both 1) deliver the electrical stimulation and 2) monitor the intracompartmental pressure. In another aspect, pressure sensor 134 may be an implantable pressure sensor that may be implanted with an electrode. In such an example, diagnostic system 100 may not require the fluid-filled catheter. It is noted that, while diagnostic system 100 may be described as comprising a probe 132 for stimulation and a pressure sensor 134, the probe 132 and/or pressure sensor 134 may be separate systems or devices. In such instances, diagnostic system 100 may communicate (e.g., via a communication network, via user interaction, etc.) with the stimulation device and/or pressure sensing device. It is further noted that the probe 132 for stimulation and the pressure sensor 134 may be comprised by one component (e.g., such as a catheter).

Where only the intracompartmental pressure is monitored, the diagnostic system 100 may automatically qualify and record the pressure for a given time interval (e.g., every minute) and present the data as a plot of the pressure over time. One advantage of this approach is to create a monitoring record without the need for a qualified clinician/nurse to be present at each monitoring event.

Figure 2:
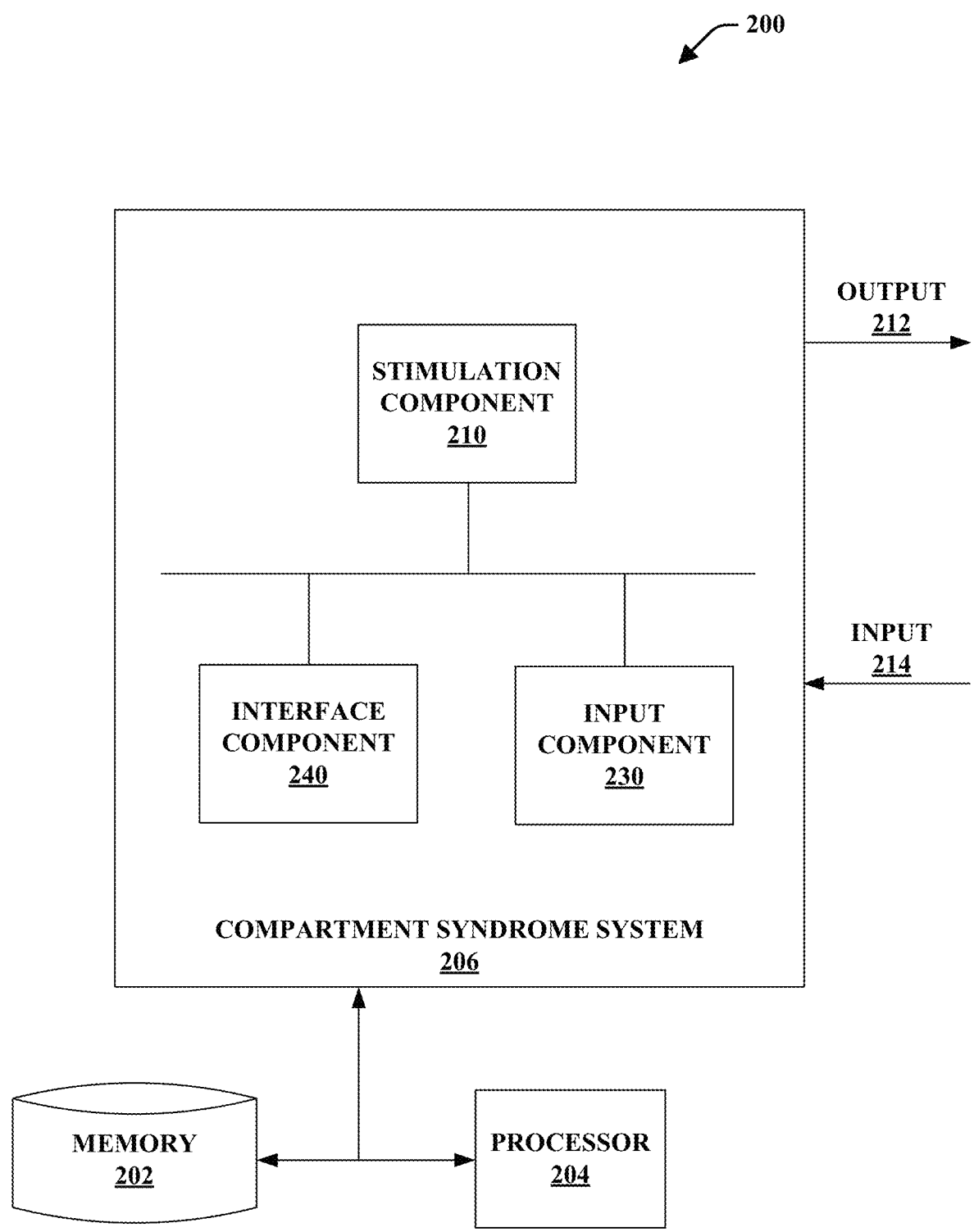
FIG. 2 is a functional block diagram of a diagnostic system for detecting compartment syndrome according to embodiments disclosed herein.

Turning to FIG. 2, there is a functional block diagram of diagnostic system 200. According to at least one embodiment, diagnostic system 200 may measure the threshold of stimulation (e.g., stimulation recruitment threshold) for muscle contractility. In another aspect, the threshold of stimulation may be measured when the pressure in the compartment is inconclusive as to whether there is a risk for the development of compartment syndrome. Diagnostic system 200 may reduce the incidence of unnecessary surgery, including fasciotomies.

Diagnostic system 200 may primarily include compartment syndrome system 206, memory 202, and processor 204. Memory 202 may be configured for storing computer executable components such as a stimulation component 210, an interface component 240, and an input component 230. Processor 204 may facilitate operation of the computer executable components. It is noted that system 200 may include one or more devices, such as an external pressure sensor device, an external stimulation device, and the like. It is further noted that one or more devices may comprise, at least in part, the various components. For instance, a single component of system 200 may be comprised by one or more devices. Further, while shown as separate or distinct components, the components of system 200 may be comprised by one or more components. It is noted that system 200 may include a plurality of compartment syndrome systems 206 that may be linked together through a network and transceivers. These compartment syndrome systems may be operatively linked with a server that may operate or otherwise communicate with the compartment syndrome systems.

It is noted that diagnostic system 100 of FIG. 1 may comprise all or part of system 200. For example, compartment syndrome system 206 may be comprised within body 110. In another aspect, compartment syndrome system 206 may generate output 212 as a stimulation signal and may receive input 214 as a response from a clinician or another system.

In embodiments, stimulation component 210 may control a stimulation device as described herein. For instance, stimulation component 210 may control parameters for stimulation, such as signal intensity, signal frequency, and the like. In an aspect, the frequency for stimulation may be within a range of frequencies that produce easily observed (e.g., by a physician and/or device) motor responses (e.g., muscle twitch). In an aspect, the range may have a lower bounds (e.g., such as about 0.5 hertz (HZ)) and an upper bounds (e.g., about 50 HZ). In another aspect, the range may be between about 0.7 HZ to about 3 HZ. It is noted that the frequency range may vary depending on desired configurations, subjects, and the like.

According to at least one embodiment, stimulation component 210 may control stimulation of a plurality of motor units. For instance, stimulation component 210 may be coupled with a plurality of electrodes that may each be in electrical contact with a disparate compartment. For example, a patient may come to a hospital after being in a serious car accident. The patient may suffer multiple injuries to different compartments and the different compartments may be monitored or checked for compartment syndrome via system 200. For instance, a doctor may connect electrodes (e.g., via percutaneous implants, probes, etc.) to target tissue regions in the compartments. The doctor may select stimulation parameters for the different compartments and system 200 may apply the parameters to the compartments via the electrodes.

Interface component 240 may communicate or control input/output devices (e.g., monitors, speakers, light emitting diode (LED) indicators, touchscreens, human interface devices, mouse, keyboard, keypad, nobs, controls, etc.) network devices, and the like. In an example, interface component 240 may receive input 214 as an input from a doctor, such as via controls 126. The doctor may provide input to configure or alter stimulation parameters, such as stimulation intensity. As described herein, the doctor may adjust the stimulation intensity to determine a threshold stimulation.

It is noted that the threshold stimulation values may be measured or determined at various times. In an aspect, the diagnostic system 100 may monitor and/or store a history of the threshold stimulation values. For instance, a doctor may check the threshold of stimulation at various times and/or in response to triggering events.

Triggering events may include time intervals (e.g., every 5, 15, 30, 45 minutes, etc.), change in pressure (e.g., increase/decrease in pressure, rate of change, etc.), change in patient's symptoms, or the like. In embodiments, interface component 240 may control an interface to generate an alert or notification indicative of a request to check a threshold of stimulation. For instance, the interface may include a monitor, a LED, a speaker, a vibration device, or the like. As such, the notification may include a visual, audible, and/or tactile notification. For instance, system 200 may generate a rendering of an image (e.g., still or moving) or text on a display (e.g., display 124), adjusting a display parameter (e.g., brightness, etc.), control a LED status indicator, generate an audible notification (e.g., voice, chime, melody, etc.); generate a vibration, or the like. It is noted that the notification may be sent to another device, such as through email, telephone networks (e.g., wired or wireless, text messages, voice messages, data messages, etc.), over intranet connections, over internet connections, or the like. In an example, system 200 may initiate a call to a nurse station. When the clinical work answers the call, a prerecorded or predetermined message may be played, or the like.

Figure 3:
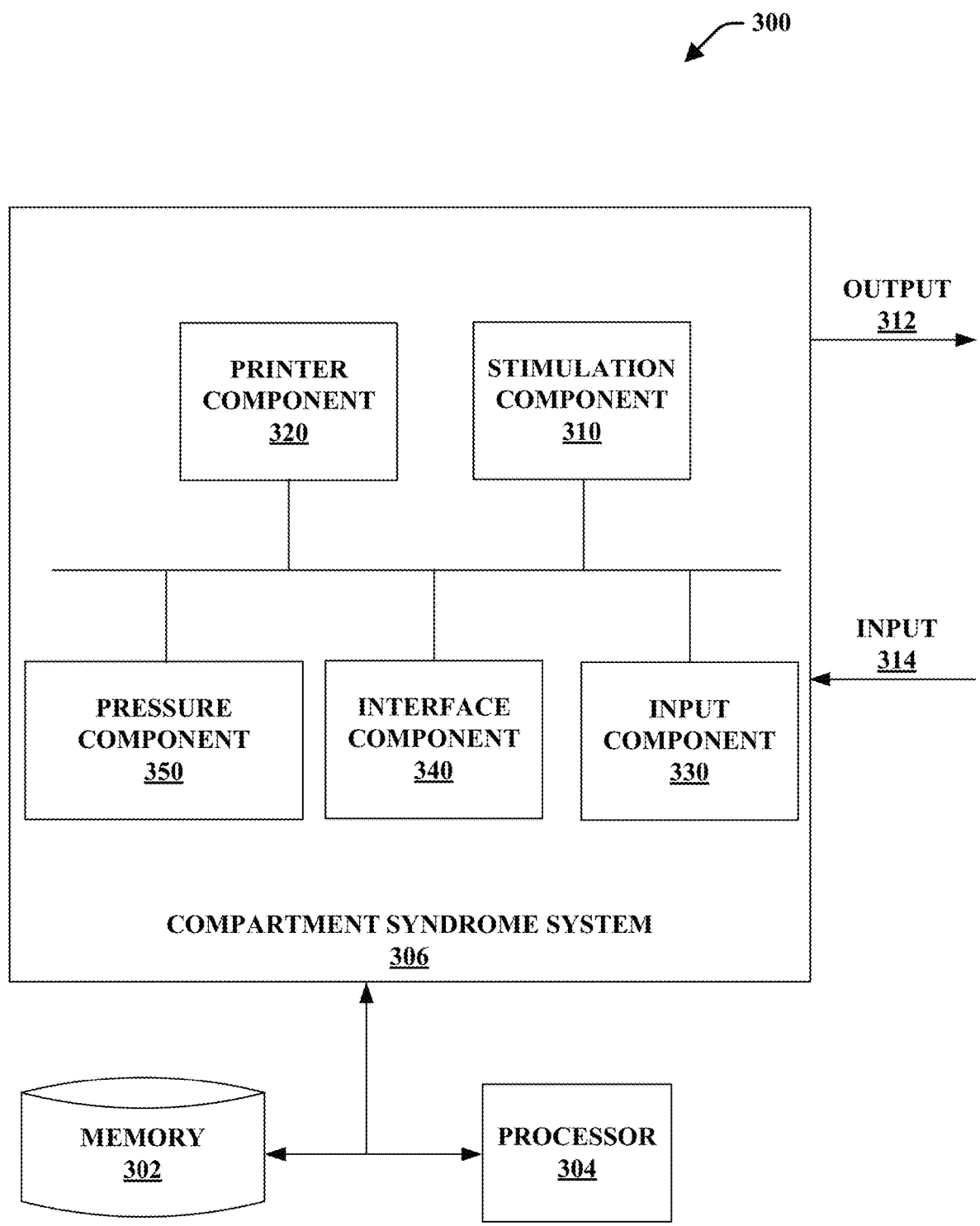
FIG. 3 is a functional block diagram of a diagnostic system for detecting compartment syndrome including a printer component according to embodiments disclosed herein.

Referring now to FIG. 3 with reference to FIGS. 1-2, depicted is a system 300 that may monitor stimulation and pressure associated with motor units in a compartment. It is noted that like named components of system 300 and other embodiments may include substantially similar functionality. For instance, stimulation component 310 may include functionality similar to stimulation component 210. Diagnostic system 300 may primarily include compartment syndrome system 306, memory 302, and processor 304. Memory 302 may be configured for storing computer executable components such as a stimulation component 310, a printer component 320, an interface component 340, a pressure component 350, and an input component 330. Processor 304 may facilitate operation of the computer executable components. It is noted that system 300 may comprise different components and may comprise one or more devices.

In an aspect, printer component 320 may control a remote printer or a printer internal to system 300, such as a printer comprised by system 100. In embodiments, a remote printer may include a printer connected to system 300 via a communication network (wireless or wired), directly connected (wirelessly or wired), or the like. In embodiments, printer component 320 may instruct the printer to print data associated with stimulation, a patient, a doctor, or the like. For instance, the printer component 320 may instruct a printer to print a graphical representation of stimulation thresholds and pressure measurements.

Pressure component 350 may measure or receive measurements associated with pressure in a compartment of a patient. For instance, a pressure component 350 may communicate with a pressure-reading device. The pressure-reading device may be comprised within system 100, for example. In another aspect, the pressure-reading device may be an external system. The pressure reading device may comprise a catheter or needle-based device (as described herein, an ultra sonic device, e.g., transmitter, etc., or other pressure sensing devices. In embodiments, the pressure-reading device and/or a doctor may provide input 314 regarding a determined pressure.

Stimulation component 310 and/or pressure component 350 may determine trends in the pressure of a compartment and/or response thresholds of motor units within the compartment. In an aspect, interface component 340 may instruct a display to render the trends. The rendering may include graphical representations, textual representations, and/or audible representations. For example, the pressure and stimulation thresholds may be rendered as plots or graphs as seen in FIG. 1. A plot may show data over a fixed period of time and/or it may scale a time axis to display all available data. It is noted that pressure and stimulation threshold may be represented in a single graph and/or in multiple graphs.

In various embodiments, input component 330 may receive input 314 from a doctor or other user. The input may be related to requests for rendering data associated with pressure and/or stimulation. For instance, a doctor may provide input to indicate a preference for representing historical information associated with the pressure and/or stimulation (e.g., timeline values, color, plot type, etc.). The preferences may be stored (e.g., in memory 202) for later use.

In another aspect, system 300 (e.g., via interface component 340) may generate alarms or indicators based on information associated with pressure and/or stimulation. For example, the alarm may be based on a pressure level exceeding a threshold pressure level, a rate of pressure increase exceeding a threshold rate, stimulation threshold exceeding a stimulation intensity threshold, a rate of stimulation threshold intensity exceeding a threshold rate, a weighted combination of various factors exceeding a threshold, or the like. In various examples, thresholds may be predetermined, set by a doctor, or dynamically determined. For instance, baseline values may be determined, such as by measurements of non-compartment syndrome areas of a patient. The baseline may then be used to dynamically determine thresholds. In an example, systems described herein may provide a stimulation signal and the threshold of stimulation intensity for visible muscle contraction may be established by stimulation of the muscle, (e.g., through the probe 132) on the involved side or by stimulation of the contralateral muscle (same muscle on the opposite side) to establish baseline threshold and then monitoring over time (e.g., a couple of hours). Likewise, pressure may be determined on the contralateral compartment. In this way, the patient may serve to generate his or her own thresholds.

As described above, system 300 may generate various alarms or alerts. In response to the alarms, the doctor may recheck pressure, stimulation thresholds, make a diagnosis, and the like.

Figure 4:
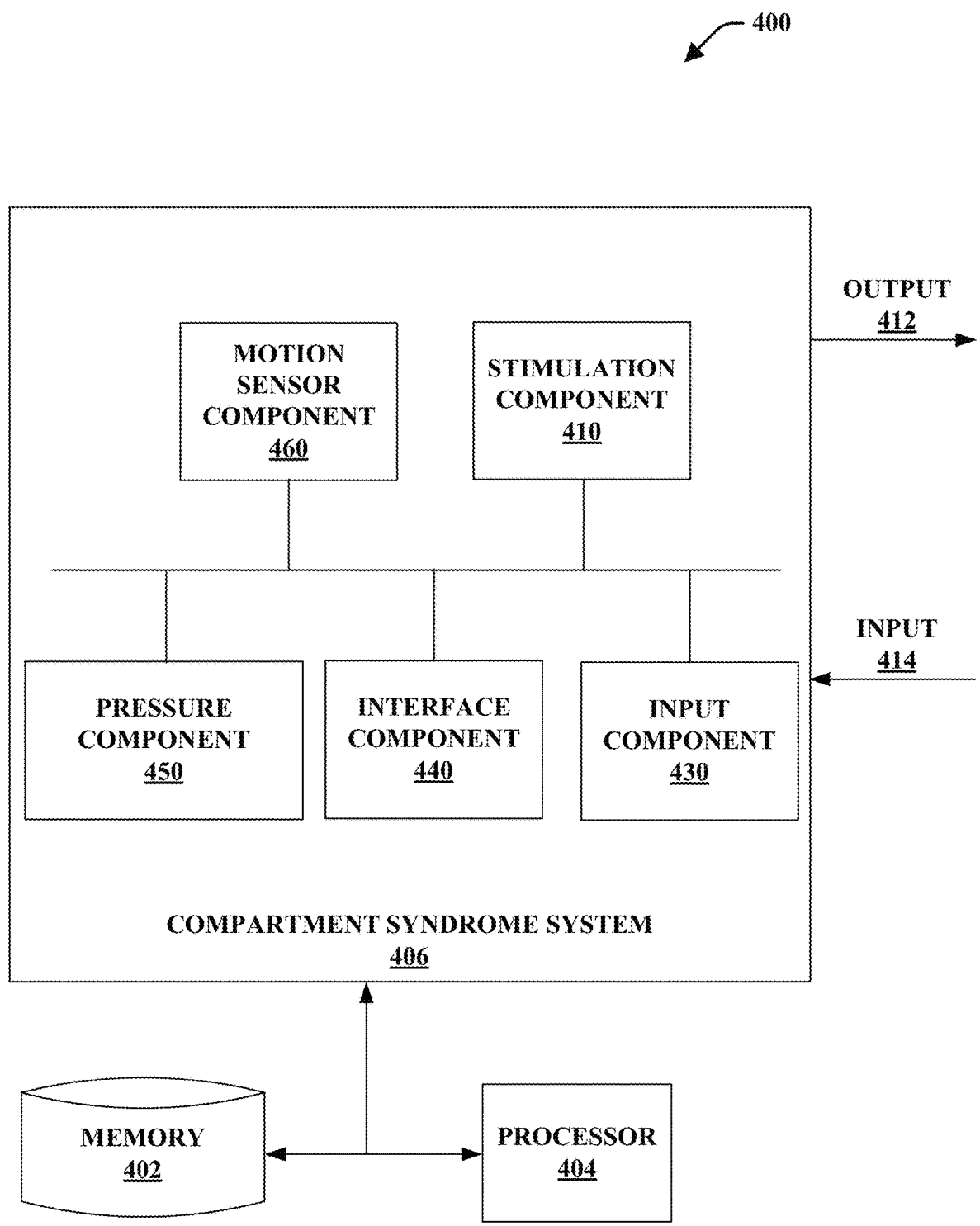
FIG. 4 is a functional block diagram of a diagnostic system for detecting compartment syndrome including a motion sensor component according to embodiments disclosed herein.

FIG. 4 is a system 400 that may monitor stimulation and pressure associated with motor units in a compartment. It is noted that like named components of system 400 and other embodiments may include substantially similar functionality. For instance, stimulation component 410 may include functionality similar to stimulation component 210 and/or 310. Diagnostic system 400 may primarily include compartment syndrome system 406, memory 402, and processor 404. Memory 402 may be configured for storing computer executable components such as a stimulation component 410, a printer component 420, an interface component 440, a pressure component 450, motion sensor component 460, and an input component 430. Processor 404 may facilitate operation of the computer executable components. It is noted that system 400 may comprise different components and may comprise one or more devices.

Motion sensor component 460 may include or control motion sensor devices, such as a muscle twitch sensor. The muscle twitch sensor may be attached to a body part associated with stimulation. The muscle twitch sensor may be attached, such as via a strap or an adhesive (e.g., tape), directly to a patient's skin and/or clothing. This sensor may comprise a strain sensor, motion sensor, and the like (e.g., an accelerometer). In an example, stimulation component 410 may periodically (or upon a triggering event) generate a stimulation signal (e.g., output 412) and may titrate the magnitude of that stimulation. Motion sensor component 460 may determine when motion of a muscle twitches. Stimulation component 410, based on the muscle twitch detection, may determine the threshold of nerve/muscle stimulation. In an aspect, this may allow fully automatic generation of the trend plot of pressure and stimulus threshold over time and any subsequent alarm generation. It is noted that a motion sensor may be disposable or reusable. It is noted that the motion sensory component 460 may utilize or comprise other devices or systems to determine a muscle twitch, such as an electromyography (EMG) electrode. An EMG electrode may use small surface electrodes or a percutaneous coiled fine wire lead (disposable and supplied sterile) to determine muscle twitch. In at least one embodiment the EMG electrode may be the same electrode delivering a stimulation signal. In another aspect, system 400 may differentiate between a stimulation signal and an electrical signal generated by volitional movement of the muscle. For instance, the system may distinguish between the signals based on a delay due to muscle response, a frequency of the signals, an intensity of the signals, or the like.

In an aspect, motion sensor component 460 may be configured to differentiate between muscle twitches caused by the simulation component 410 and other movements (e.g., movements cause by a doctor or a patient). For instance, motion sensor component 460 may determine a pattern associated with a signal from a motion sensor device. Based on this pattern, the motion sensory component 460 may differentiate between stimulus induced motion and other motions. In another aspect, the motion sensory component 460 may distinguish between motions based in part on a timing associated with stimulation component 410. In an example, motion sensor component 460 may monitor motion only during stimulation events or times near stimulation events. For instance, system 400 may synchronize stimulation and response measurements, may determine time correlations, or the like.

Figure 5:
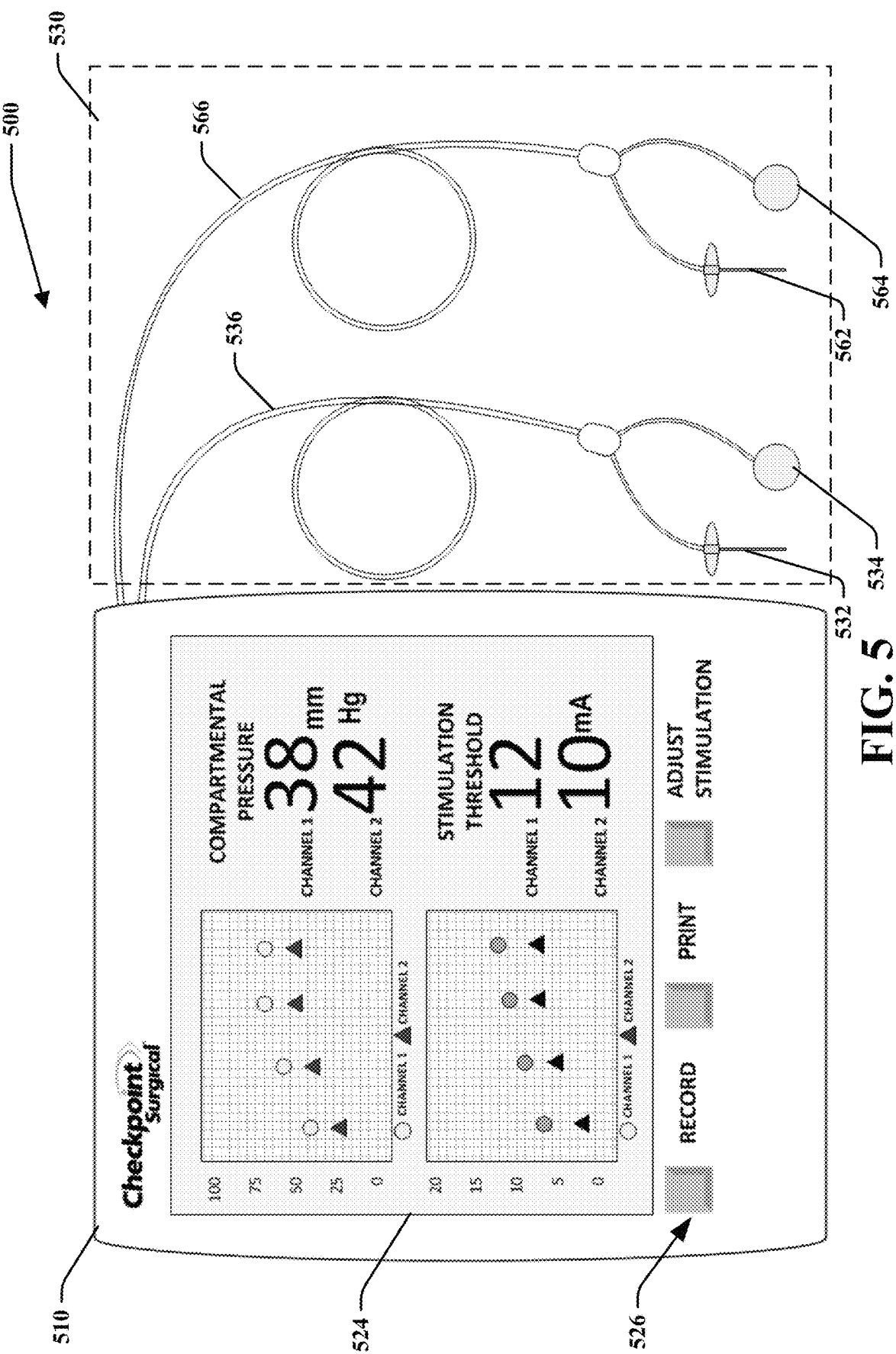
FIG. 5 is multi-channel diagnostic system for detecting compartment syndrome including pressure sensors according to embodiments disclosed herein.
Figure 6:
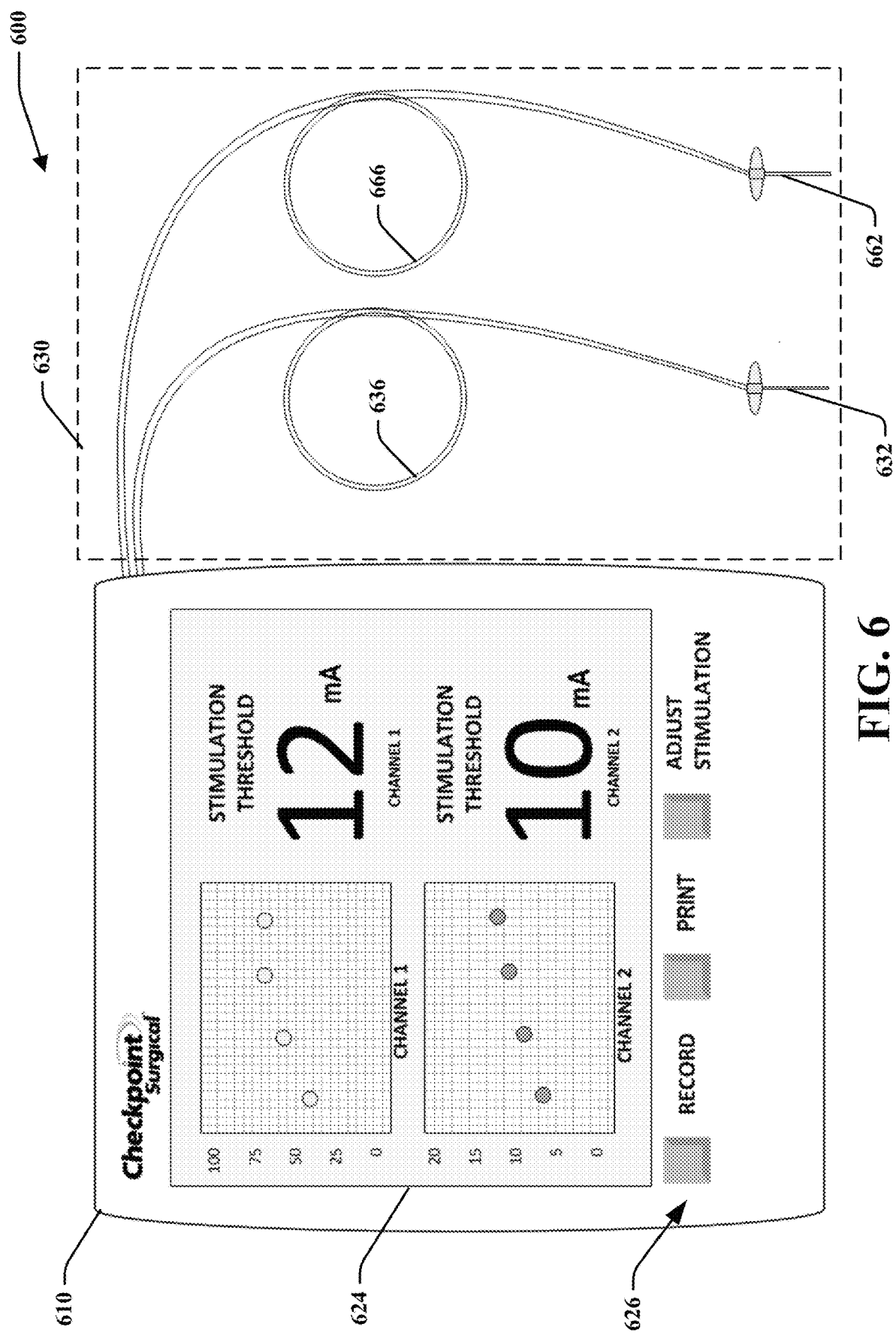
FIG. 6 is multi-channel diagnostic system for detecting compartment syndrome according to embodiments disclosed herein.

FIGS. 5 and 6 depict multi-channel diagnostic systems 500 and 600 as described herein. Diagnostic systems 500 and 600 may be used to diagnose one or more compartments (and/or patients) and in particular to indicate whether the one or more compartments has compartment syndrome and the severity of the compartment pressure. While diagnostic systems 500 and 600 are shown as dual channel systems, it is noted that diagnostic systems 500 and 600 may comprise a different number of channels. It is further noted that diagnostic systems 500 and 600 may comprise other systems, such as systems 100, 200, etc. For instance, diagnostic system 100 may be operatively attached with various numbers of leads, types of sensors, or the like.

Diagnostic system 500 may include a body 510 comprising various components (e.g., power source, memory, processor, etc.) and circuitry. The body 510 may be connected (removably or irremovably) to a stimulation interface 530 comprising a signal path (e.g., wire, etc.) 536 coupled (removably or irremovably) to a probe 532 and a pressure sensor 534. Further, stimulation interface 530 may comprise signal path (e.g., wire, etc.) 566 coupled (removably or irremovably) to a probe 562 and a pressure sensor 564.

Diagnostic system 600 may include a body 610 comprising various components (e.g., power source, memory, processor, etc.) and circuitry. The body 610 may be connected (removably or irremovably) to a stimulation interface 630 comprising a signal path (e.g., wire, etc.) 636 coupled (removably or irremovably) to a probe 632. Further, stimulation interface 630 may comprise signal path (e.g., wire, etc.) 666 coupled (removably or irremovably) to a probe 662.

Each signal path of systems 500 and 600 may represent a distinct channel. It is noted that, while diagnostic system 500 is depicted to comprise channels having both probes and pressure sensors, it is noted that the channels may comprise different components. For example, single path 536 may not include pressure sensor 534. Similarly, diagnostic system 600 may include channels that comprise different components (e.g., single path 666 may include a pressure sensor).

In another example, a doctor may insert probe 532 into a patient to monitor a first compartment of (e.g., a compartment of a left leg) and may attach pressure sensor 534 to the first compartment of the patient. The first compartment may be a compartment suspected of compartment syndrome. The doctor may then insert probe 562 into the patient to monitor a second compartment of (e.g., a compartment of a right leg) and may attach pressure sensor 564 to the patient for monitoring pressure of the second compartment. The second compartment may be a compartment that is healthy or not suspected of compartment syndrome. In some embodiments, the second compartment may be a contralateral muscle of the first muscle (e.g., mirror muscle on the opposite leg). In such an example, a baseline may be established for the patient.

In embodiments, each channel may be attached to different users or different compartments. For instance, a doctor may insert probe 532 into a first patient and may attach pressure sensor 534 to the first patient. The doctor may also insert probe 562 into a second patient and may attach pressure sensor 564 to the second patient. Such can allow for monitoring of multiple patients with only one device.

It is noted that systems 500 and 600 may determine whether the channels are utilized for a single compartment/patient or for a plurality of compartments/patients. The number of compartments/patients may be determined based on received user input (e.g., input from a doctor), such as through controls, switches, knobs, etc. Based on this determination, systems 500 and 600 may determine whether to set baselines and how to control displays 524 and/or 624. For example, if multiple patients are being monitored or diagnosed, the display may provide two charts pertaining to each channel. If a single patient is being monitored, the display may provide a single chart for the concerned compartment. As depicted in FIG. 5, the display 524 may provide a chart for pressure of each channel, and may provide a chart for stimulation thresholds of each channel. It is noted that display 524/624 may be configured to render various other outputs based on whether a single patient is monitored or whether multiple patients are monitored. For instance, the display may render an adjusted stimulus parameter and the parameter may be plotted as the stimulus current amplitude with a fixed pulse duration, the stimulus pulse duration at a fixed current amplitude, or the charge of the stimulus pulse. It is noted that a plot may be over a specific period of time, may represent the complete history of stimulation/pressure, or the like.

In another aspect, the systems 500 and 600 may be designed for a specific use and may not determine whether the channels are utilized for a single patient or for a plurality of patients.

Figure 7:
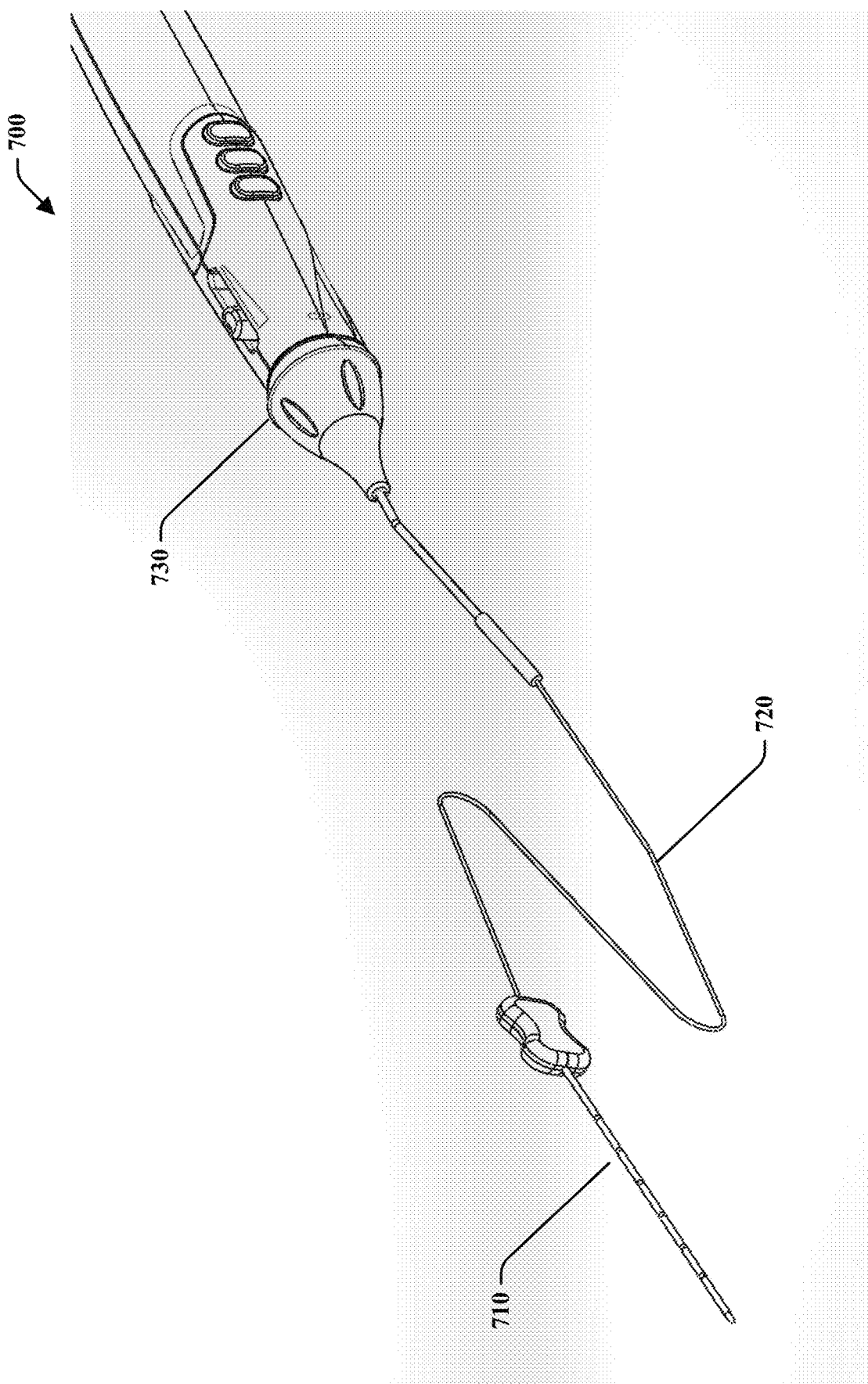
FIG. 7 is a percutaneous lead for a diagnostic system according to embodiments disclosed herein.
Figure 8:
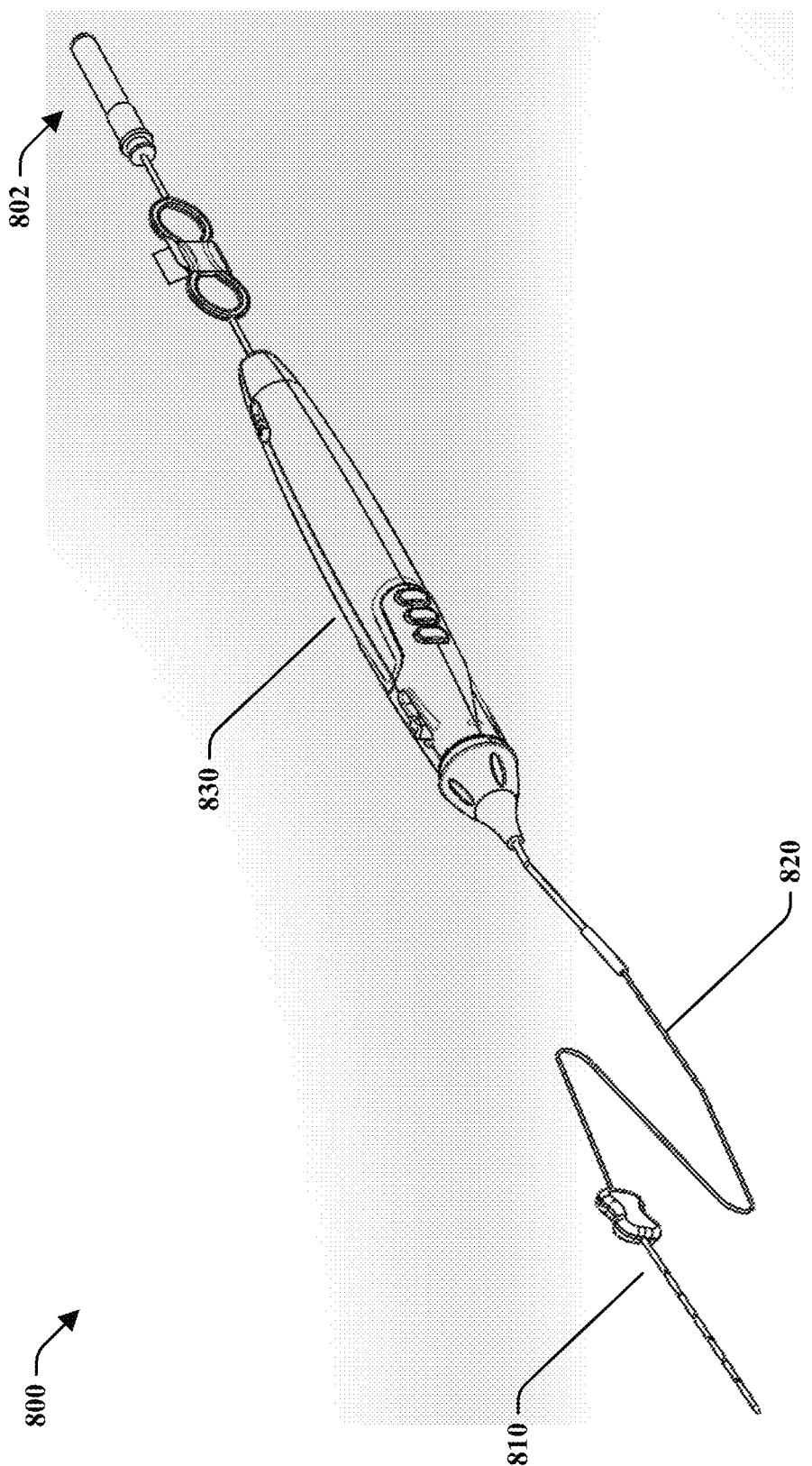
FIG. 8 is a percutaneous lead for a diagnostic system with return electrode and a connection to a stimulator according to embodiments disclosed herein.

FIGS. 7 and 8 depict percutaneous needle systems 700 and 800, which may stimulate a compartment via percutaneous needles 710 and 810. Needles 710 and 810 may be connected to a body 730/830 via leads 720/820. It is noted that various systems may utilize percutaneous needles 710 and 810. Further, system 800 is depicted as including return electrode 802.

As described herein, various systems and methods may provide objective evidence of muscle viability and contractility and would allow detection of a trend toward diminution of muscle excitability, indicative of ischemia, over time. The device may sound an audible alarm or display a visual indicator when the threshold is increased to a predetermined level indicating risk of tissue damage. Unlike compartment pressure measurements, this would be a direct measurement of muscle function, which is the primary issue of concern with compartment syndrome.

The method for detecting compartment syndrome may include identifying a patient with an injury that may result in compartment syndrome. According to the method, the patient may be screened for symptoms associated with compartment syndrome, including, but not limited to pain out of proportion to the injury, paresthesias (numbness), paralysis (loss of contractility), pallor (loss of pulses), poikilothermia, skin tenseness, and vascular congestion. If, based on type of injury, the presentation of symptoms or both, it is believed that compartment syndrome may result, the patient can be monitored to determine the likelihood of compartment syndrome developing.

Monitoring may include measuring the compartment pressure in the affected muscle. Pressure may be measured by any appropriate means for measuring compartment pressure. For example, pressure may be measured by a needle and a manometer or pressure transducer.

If the measured pressure is greater than 35 mm Hg or within 20 mm Hg of diastolic pressure, the risk of developing compartment syndrome may be significant and fasciotomy may be warranted.

If the measured pressure is less than 35 mm Hg and greater than about 20 mm Hg, or if the patient is exhibiting symptoms that indicate the possibility that compartment syndrome might develop, the patient can be monitored using a simulation device. Alternatively, a patient may be monitored with a stimulation device without first measuring the compartment pressure.

The method for determining the risk of developing compartment syndrome includes assessing common factors associated with compartment syndrome. Factors to be considered when assessing the risk of developing compartment syndrome may include the timeline of changes (e.g., muscle responses, ischemia, biological substances, irreversible damage, etc.) associated with compartment syndrome. The timeline of changes in muscle response in relationship to progression of ischemia may provide insight into when muscle activation is lost relative to when irreversible damage occurs. For example, if muscle contraction is lost quickly (within 1 hour) and irreversible damage does not begin until later (5 hours), there may be a sufficient window (e.g., 4 hours) in which a fasciotomy can be performed to prevent damage. However, if muscle contraction slowly fades over several hours and irreversible damage is occurring in parallel, then the muscle response may not provide a warning soon enough to prevent damage.

The effects of compartment syndrome are time dependent. If, after the fasciotomy is performed, the muscle appears to bulge out of the incision, then it is likely that the fasciotomy was needed. If, on the other hand, the muscle appears healthy, it is possible that the fasciotomy was not necessary or that the fasciotomy was performed early enough to prevent ischemia and interstitial edema.

Figure 9:
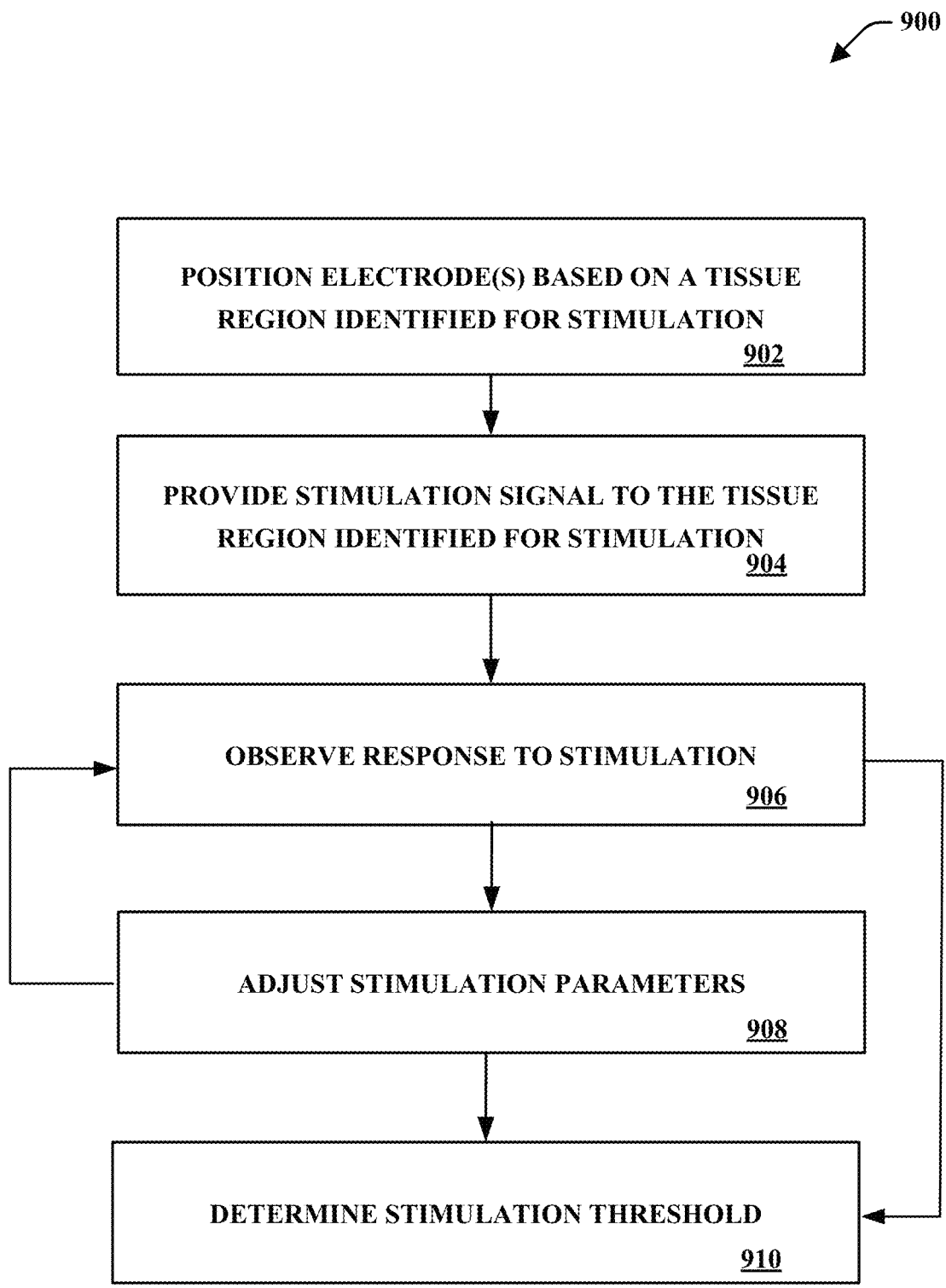
FIG. 9 is a method for determining a stimulus threshold according to embodiments disclosed herein.
Figure 10:
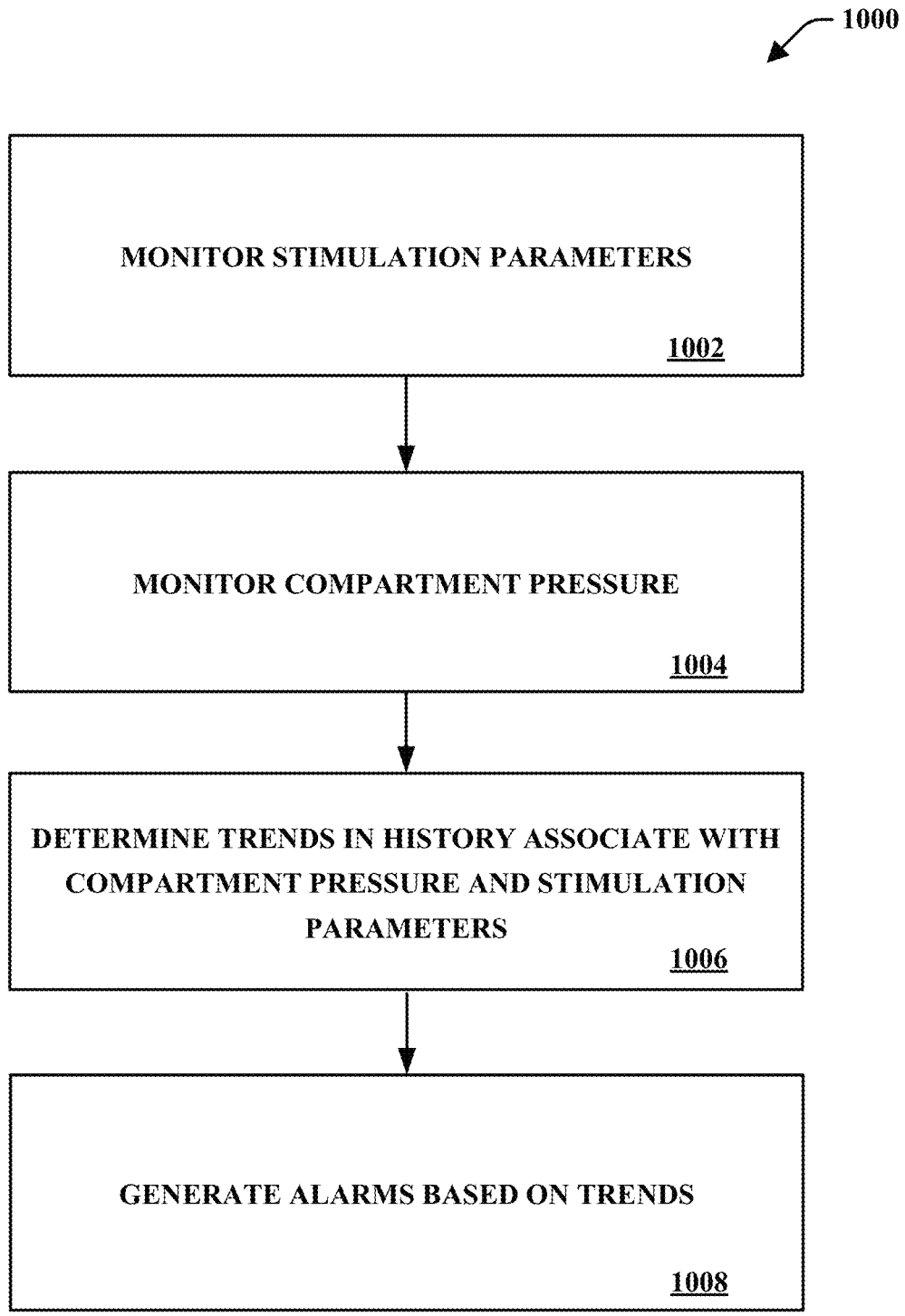
FIG. 10 is a method for diagnosing compartment syndrome according to embodiments disclosed herein.
Figure 11:
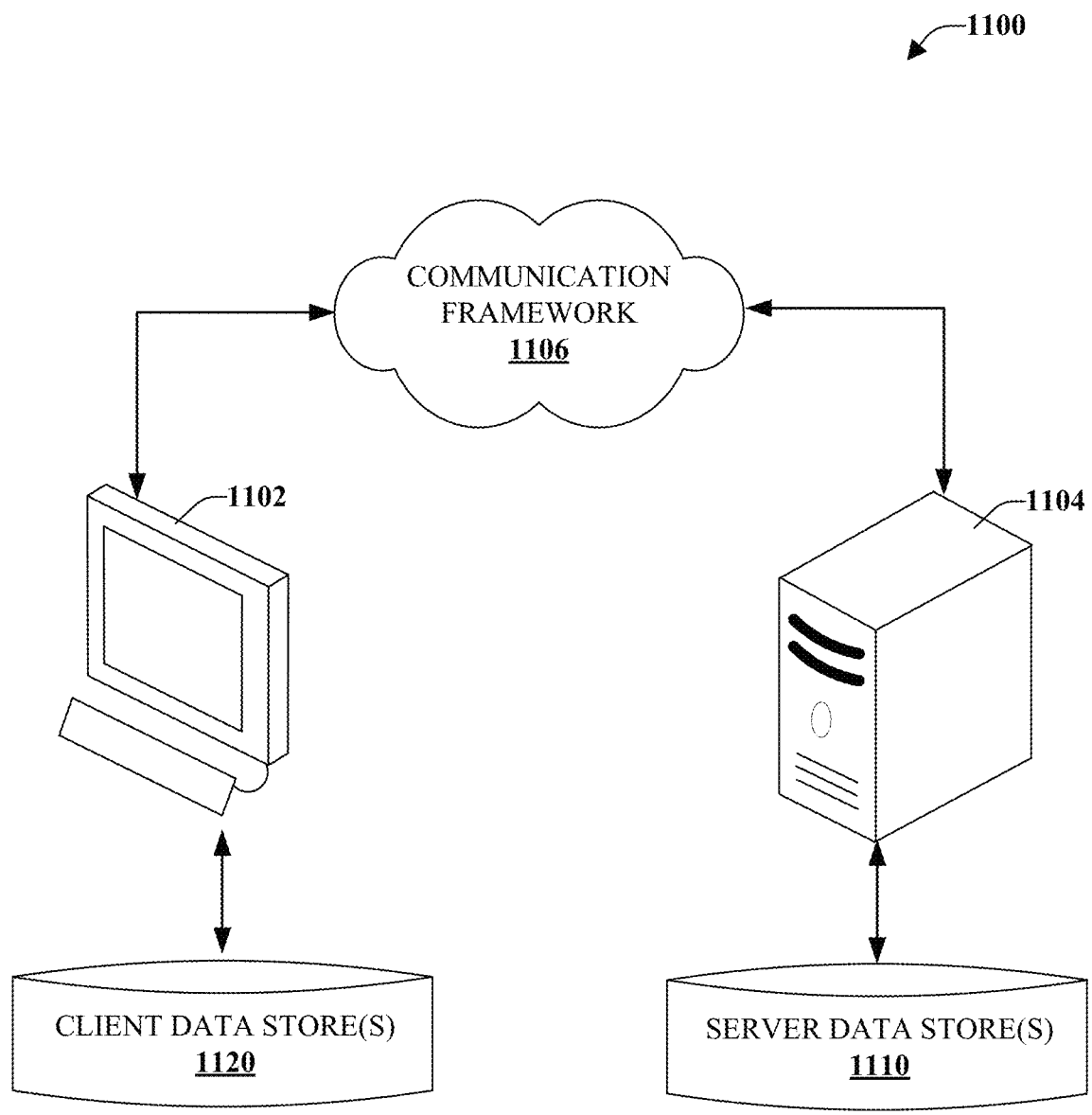
FIG. 11 is an environmental diagram of an exemplary communication system according to embodiments disclosed herein.

In view of the subject matter described herein, methods that may be related to various embodiments may be better appreciated with reference to the flowcharts of FIGS. 9-11. While the methods are shown and described as a series of blocks, it is noted that associated methods or processes are not limited by the order of the blocks. It is further noted that some blocks and corresponding actions may occur in different orders or concurrently with other blocks. Moreover, different blocks or actions may be utilized to implement the methods described hereinafter. Various actions may be completed by one or more of users, mechanical machines, automated assembly machines (e.g., including one or more processors or computing devices), or the like.

FIG. 9 depicts an exemplary flowchart of non-limiting method 900 associated with a diagnosis system, according to various aspects of the subject disclosure. As an example, method 900 may determine a stimulation threshold associated with a motor unit.

At 902, a doctor may position electrode(s) based on a tissue region identified for stimulation. The tissue region may be a region selected for stimulation (e.g., through muscle or neural tissue) of motor units within a compartment. As described herein, the compartment may be a compartment at risk of compartment syndrome or a contralateral compartment.

At 904, a system may provide a stimulation signal to the tissue region identified for stimulation. At 906, the system or a doctor may observe the response to stimulation. The response may be actuation of a motor unit or no actuation of a motor unit. At 908, a system or a doctor may adjust stimulation parameters based at least in part on the response observed at 906. It is noted that the stimulation, observation, and adjustment may be iterated one or more times. For example, the iteration may continue until a stimulation threshold is determined at 910, such as by a system or a doctor.

FIG. 10 depicts an exemplary flowchart of non-limiting method 1000 associated with a diagnosis system, according to various aspects of the subject disclosure. As an example, method 1000 may determine a stimulation threshold associated with a motor unit.

At 1002, a doctor or a system may monitor stimulation parameters. In an aspect, the stimulation parameters may be stored in a memory. At 1004, a doctor or a system may monitor compartment pressure. It is noted that the compartment pressure may be stored in memory. It is noted that some or all of the stimulation and/or pressure parameters may be stored in memory. For instance, system 100 or another system may monitor the parameters over a certain time period (e.g., over the past hour, 30 minutes, etc.).

At 1006, a doctor or a system may determine trends in history associated with compartment pressure and stimulation, as described herein. The trends may indicate changes in pressure/stimulation parameters, rates of change, or the like.

At 1008, a system may generate alarms as described herein. The alarms may be audible alarms, visual alarms, tactile alarms, or the like. For example, the system may generate alarms based on the trends, such as an alarm based on a change in pressure/stimulation parameters exceeding a threshold rate of change, pressure/stimulation parameters exceeding a threshold level, or the like.

Example

An 11-year-old girl sustained a type III supracondylar elbow fracture. The patient underwent closed reduction and internal fixation of the fracture. However, postoperatively she complained of severe and unremitting pain in the arm. The pain was so severe that readmission to the hospital for pain control was necessary and compartment syndrome was considered. Compartment pressures were measured in the dorsal and volar compartments. The pressure was found to be in the range from the high teens to the mid twenties.

The clinical observation of severe pain and the ambiguous pressure readings indicated that the patient might be a risk for developing compartment syndrome.

Muscle contractility was measured directly using a stimulator, such as a CHECKPOINT stimulator. Placing the ground in the subcutaneous tissues, an insulated anesthesia block needle was connected to the stimulator and inserted percutaneously in the superficial and deep compartments.

Good stimulation, as evidenced by strong finger flexion, could be elicited in the 2 mA range. Stimulation in the low 20 mA range produced a vigorous, tetanic contraction of the flexor muscles, indicating muscle viability and normal function. The stimulator was next used to define the threshold at which stimulation first occurred by gradually increasing the stimulus intensity and noting the point at which finger motion was first observed.

The finding of normal muscle excitability suggested that a subcutaneous fasciotomy with a 1 cm incision, placed in an inconspicuous location, rather than a standard fasciotomy through a long elbow-to-wrist incision would be a proper course of treatment.

Post-operatively, the patient's pain resolved and at the next follow-up office visit one week after the surgery, the patient had full finger motion, no pain and normal motor and sensory function.

Thus, a percutaneous stimulator was used to directly test and assess muscle viability and excitability in a patient at risk for developing compartment syndrome with ambiguous physical findings and pressure measurements. Without the stimulator, a full fasciotomy would have been necessary to avoid the risk of missing a compartment syndrome. Such a technique might help avoid unnecessary fasciotomies, with the attendant scarring and risks associated with multiple surgical procedures.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

Figure 12:
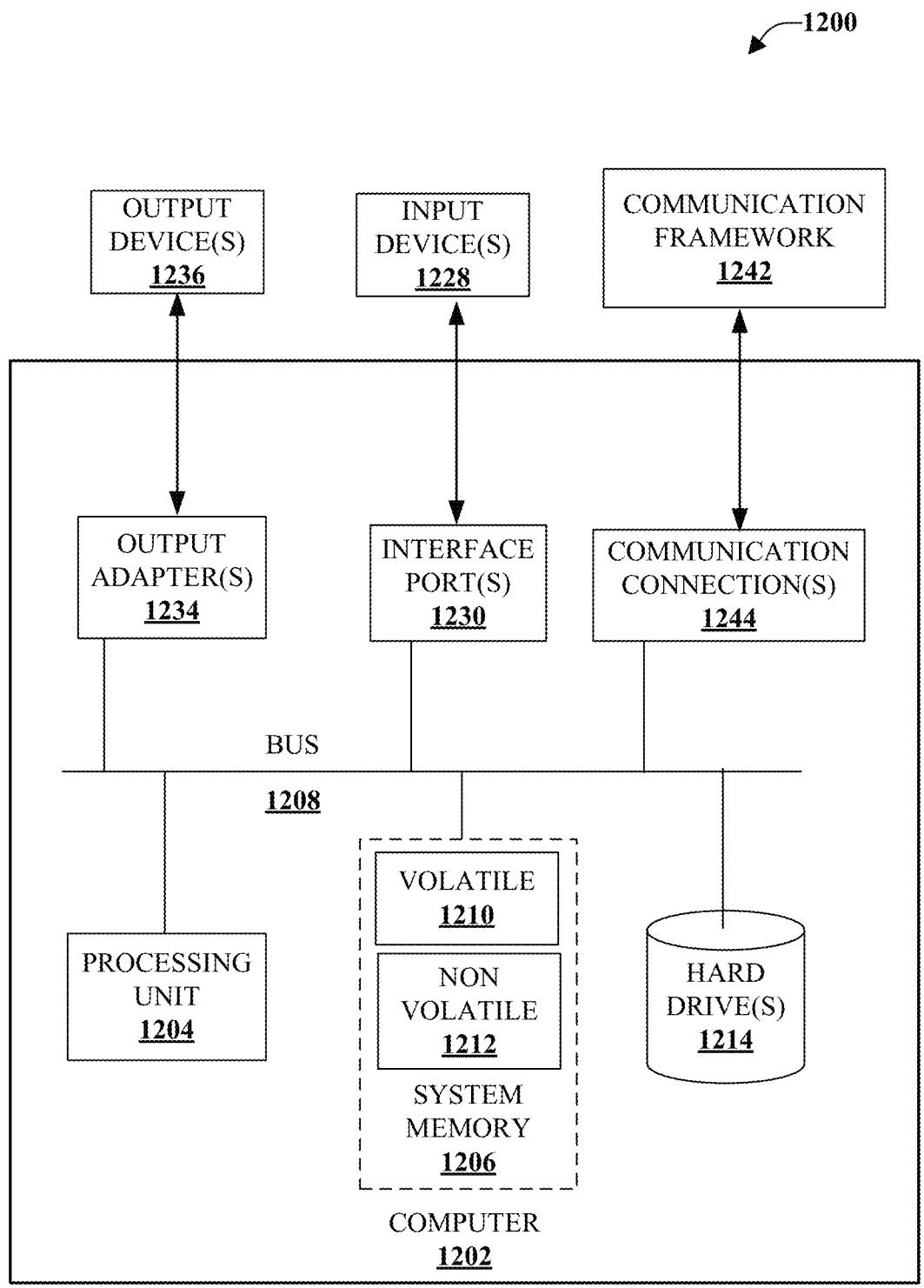
FIG. 12 is a block diagram of a functional computer system according to embodiments disclosed herein.

What has been described above may be further understood with reference to the following figures. FIGS. 11 and 12 provide exemplary operating environments or systems capable of implementing one or more systems, apparatuses, or processes described above. FIGS. 11 and 12 are not intended to limit the scope of such systems, apparatuses, or processes. By way of example, computing environment 1100 may refer to one or more embodiment of the various embodiments described with reference to the above figures. However, variations to computing environment 1100 may be obvious to achieve aspects or processes described herein.

FIG. 11 is a schematic diagram of a computing environment 1100 in accordance with various disclosed aspects. It is noted that environment 1100 may include various other components or aspects. As depicted, system 1100 may include one or more client(s) 1102 (e.g., stimulation device and/or a device connected to the stimulation device), one or more server(s) 1104, one or more client data store(s) 1120, one or more server data store(s) 1110, and a communication framework 1106.

While depicted as a desktop computer(s), client(s) 1102 may include various other devices that may comprise hardware and/or software (e.g., program threads, processes, computer processors, non-transitory memory devices, etc.). In an example, client(s) 1102 may include laptop computers, smart phones, tablet computers, diagnostic devices, pressure sensors, stimulation device, medical devices, etc. The client(s) 1102 may include or employ various aspects disclosed herein. For example, client(s) 1102 may include or employ all or part of various systems (100, 200, 300, etc.) and processes (e.g., method 900, 1000, etc.) disclosed herein. In an embodiment, client(s) 1102 may include a stimulation device having a communication component configured for communicating via communication framework 1106. It is noted that the communication component may include wireless or wired communications capabilities as described herein.

Likewise, server(s) 1104 may include various devices that may comprise hardware and/or software (e.g., program threads, processes, computer processors, non-transitory memory devices, etc.). Server(s) 1104 may include or employ various aspects disclosed herein. For example, server(s) 1104 may include or employ all or part of various systems (100, 200, 300, etc.) and processes (e.g., method 900, 1000, etc.) disclosed herein. It is noted that server(s) 1104 and client(s) 1102 may communicate via communication framework 1106. In an exemplary communication, client(s) 1102 and server(s) 1104 may utilize packeted data (e.g., data packets) adapted to be transmitted between two or more computers. For instance, data packets may include coded information associated with a stimulation process, diagnostic process, pressure-monitoring process, or the likes.

Communication framework 1106 may comprise various network devices (e.g., access points, routers, base stations, etc.) that may facilitate communication between client(s) 1102 and server(s) 1104. It is noted various forms of communications may be utilized, such as wired (e.g., optical fiber, twisted copper wire, etc.) and/or wireless (e.g., cellular, Wi-Fi, near field communication, etc.) communications.

In various embodiments, client(s) 1102 and server(s) 1104 may respectively include or communicate with one or more client data store(s) 1120 or one or more server data store(s) 1110. The data stores may store data local to client(s) 1102 or server(s) 1104.

In at least one embodiment, a client of client(s) 1102 may transfer data describing a stimulus parameter, a user response to stimulation, a time of stimulation, or the likes to a server of server(s) 1104. The server may store the data and/or employ processes to alter the data. For example, the server may transmit the data to other clients of client(s) 1102, such as a physician's or facility's desktop computer.

FIG. 12 is a block diagram of a computer system 1200 that may be employed to execute various disclosed embodiments. It is noted that various components may be implemented in combination with computer executable instructions, hardware devices, and/or combinations of hardware and software devices that may be performed by computer system 1200.

Computer system 1200 may include various components, hardware devices, software, software in execution, and the likes. In embodiments, computer system 1200 may include computer 1200. Computer 1200 may include a system bus 1208 that couples various system components. Such components may include a processing unit(s) 1204, system memory device(s) 1206, disk storage device(s) 1214, sensor(s) 1235, output adapter(s) 1234, interface port(s) 1230, and communication connection(s) 1244. One or more of the various components may be employed to perform aspects or embodiments disclosed herein.

Processing unit(s) 1204 may comprise various hardware processing devices, such as single core or multi-core processing devices. Moreover, processing unit(s) 1204 may refer to a "processor," "controller," "computing processing unit (CPU)," or the likes. Such terms generally relate to a hardware device. Additionally, processing unit(s) 1204 may include an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or the likes.

System memory 1206 may include one or more types of memory, such volatile memory 1210 (e.g., random access memory (RAM)) and non-volatile memory 1212 (e.g., read-only memory (ROM)). ROM may include erasable programmable ROM (EPROM), electrically erasable programmable ROM (EEPROM). In various embodiments, processing unit(s) 1204 may execute computer executable instructions stored in system memory 1206, such as operating system instructions and the likes.

Computer 1202 may also be one or more hard drive(s) 1214 (e.g., EIDE, SATA). While hard drive(s) 1214 are depicted as internal to computer 1202, it is noted that hard drive(s) 1214 may be external and/or coupled to computer 1202 via remote connections. Moreover, input port(s) 1230 may include interfaces for coupling to input device(s) 1228, such as disk drives. Disk drives may include components configured to receive, read and/or write to various types of memory devices, such as magnetic disks, optical disks (e.g., compact disks and/or other optical media), flash memory, zip drives, magnetic tapes, and the likes.

It is noted that hard drive(s) 1214 and/or other disk drives (or non-transitory memory devices in general) may store data and/or computer-executable instructions according to various described embodiments. Such memory devices may also include computer-executable instructions associated with various other programs or modules. For instance, hard drives(s) 1214 may include operating system modules, application program modules, and the likes. Moreover, aspects disclosed herein are not limited to a particular operating system, such as a commercially available operating system.

Input device(s) 1228 may also include various user interface devices or other input devices, such as sensors (e.g., microphones, pressure sensors, light sensors, etc.), scales, cameras, scanners, facsimile machines, and the likes. A user interface device may generate instructions associated with user commands. Such instructions may be received by computer 1202. Examples of such interface devices include a keyboard, mouse (e.g., pointing device), joystick, remote controller, gaming controller, touch screen, stylus, and the likes. Input port(s) 1230 may provide connections for the input device(s) 1228, such as via universal serial ports USB ports), infrared (IR) sensors, serial ports, parallel ports, wireless connections, specialized ports, and the likes.

Output adapter(s) 1234 may include various devices and/or programs that interface with output device(s) 1236. Such output device(s) 1236 may include LEDs, computer monitors, touch screens, televisions, projectors, audio devices, printing devices, or the likes.

In embodiments, computer 1202 may be utilized as a client and/or a server device. As such, computer 1202 may include communication connection(s) 1244 for connecting to a communication framework 1242). Communication connection(s) 1244 may include devices or components capable of connecting to a network. For instance, communication connection(s) 1244 may include cellular antennas, wireless antennas, wired connections, and the likes. Such communication connection(s) 1244 may connect to networks via communication framework 1242. The networks may include wide area networks, local area networks, facility or enterprise wide networks (e.g., intranet), global networks (e.g., Internet), satellite networks, and the likes. Some examples of wireless networks include Wi-Fi, Wi-Fi direct, BLUETOOTH™, Zigbee, and other 802.XX wireless technologies. It is noted that communication framework 1242 may include multiple networks connected together. For instance, a Wi-Fi network may be connected to a wired Ethernet network.

The terms "component," "module," "system," "interface," "platform," "service," "framework," "connector," "controller," or the like are generally intended to refer to a computer-related entity. Such terms may refer to at least one of hardware, software, or software in execution. For example, a component may include a computer-process running on a processor, a processor, a device, a process, a computer thread, or the likes. In another aspect, such terms may include both an application running on a processor and a processor. Moreover, such terms may be localized to one computer and/or may be distributed across multiple computers.

What has been described above includes examples of the present specification. It is, of course, not possible to describe every conceivable combination of components or methodologies for purposes of describing the present specification, but it is noted that many further combinations and permutations of the present specification are possible. Each of the components described above may be combined or added together in any permutation to define a stimulation device or method. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

What is claimed is:

1. A compartment syndrome diagnosis device, comprising:
a percutaneous probe comprising an electrode;
a lead operatively connected with the percutaneous probe; and a hand-held electrical stimulation device, wherein the hand-held electrical stimulation device generates a stimulus signal intended to elicit a visible and/or palpable muscle contraction of a motor unit of a compartment and the hand-held electrical stimulation device monitors at least one stimulation parameter associated with a stimulation threshold of the motor unit of the compartment, wherein the hand-held electrical stimulation device operatively delivers, based on the stimulation parameter, a stimulation signal to the motor unit via the electrode.

2. The device of claim 1, wherein the percutaneous probe is configured to be at least partially implanted into a tissue region.

3. The device of claim 1, wherein the electrode is configured for delivering unipolar stimulation to the motor unit.

4. The device of claim 1, further comprising a return electrode coupled to the hand-held electrical stimulation device, the return electrode configured to provide a return path for the stimulation signal.

5. The device of claim 1 further comprising at least one control device configured to receive an input related to the stimulation signal.

6. The device of claim 1, wherein the at least one control device comprises at least one of a user input device, a muscle twitch sensor operatively coupled to a patient receiving the electrical stimulation, or an electromyograph electrode comprising at least one of a surface electrode or a percutaneous lead.

7. The device of claim 6, wherein the at least one control device generates a notification indicative of at least one of a prompt to a user to initiate iterating alteration of the stimulus signal, upon the at least one stimulation parameter exceeding a threshold, a rate of alteration of the at least one stimulation parameter exceeding a threshold rate, or a weighted combination thereof.

8. The device of claim 7, wherein the at least one control device generates notification as at least one of an audible notification, visual notification, a tactile notification, or a communication notification sent through a communications network to a user device.

9. The device of claim 1, wherein the stimulation parameter for stimulation of the motor unit comprises a stimulation signal comprising within a range of frequency, wherein the range is greater than about 0.5 to less than about 50 hertz.

10. The device of claim 9, wherein the range is greater than about 0.7 to less than about 3 hertz.

11. The device of claim 1, further comprising a pressure sensor configured to measure interstitial pressure within the compartment.

12. The device of claim 11, wherein the percutaneous probe further comprises the pressure sensor.

13. A compartment syndrome diagnosis device, comprising:
a hand-held stimulation device that generates a stimulation signal;
a percutaneous probe operatively in communication with a motor unit suspected of compartment syndrome, wherein the stimulation component stimulates the motor unit via the percutaneous probe and based on the stimulation signal, wherein the stimulation signal comprises parameters intended to elicit a palpable and/or visible muscle contraction of the motor unit; and
a sensor configured to measure a pressure of a compartment comprising the motor unit.

14. The device of claim 13 further comprising a display device indicating stimulation parameters associated with stimulation and pressure parameters.

15. The device of claim 14 further comprising a memory operatively storing a history of the stimulation parameters.

16. The device of claim 13, wherein the sensor comprises an intermuscular pressure sensing component.

17. The device of claim 13 further comprising a motion sensor operatively measuring the palpable and/or visible muscle contraction.

* * * * *